US011054411B2

(12) United States Patent
Linssen et al.

(10) Patent No.: US 11,054,411 B2
(45) Date of Patent: Jul. 6, 2021

(54) METHOD OF CONTROLLING A BLOOD ANALYZER FOR MEASURING PLATELETS

(71) Applicant: Sysmex Corporation, Kobe (JP)

(72) Inventors: Jo Linssen, Kerkrade (NL); Pieter Steenhuis, Hamburg (DE)

(73) Assignee: Sysmex Corporation, Hyogo (JP)

( * ) Notice: Subject to any disclaimer, the term of this patent is extended or adjusted under 35 U.S.C. 154(b) by 538 days.

(21) Appl. No.: 15/622,734

(22) Filed: Jun. 14, 2017

(65) Prior Publication Data

US 2017/0363610 A1  Dec. 21, 2017

(30) Foreign Application Priority Data

Jun. 17, 2016  (EP) .................................. 16174984

(51) Int. Cl.
| | |
|---|---|
| *G01N 33/49* | (2006.01) |
| *G01N 35/00* | (2006.01) |
| *G01N 15/14* | (2006.01) |
| *G01N 15/12* | (2006.01) |
| G01N 15/00 | (2006.01) |
| G01N 15/10 | (2006.01) |
| G01N 21/64 | (2006.01) |
| G01N 27/06 | (2006.01) |

(52) U.S. Cl.
CPC ............. *G01N 33/49* (2013.01); *G01N 15/12* (2013.01); *G01N 15/1459* (2013.01); *G01N 35/00623* (2013.01); *G01N 35/00871* (2013.01); *G01N 21/6428* (2013.01); *G01N 27/06* (2013.01); *G01N 2015/0084* (2013.01); *G01N 2015/1006* (2013.01); *G01N 2015/1037* (2013.01);

(Continued)

(58) Field of Classification Search
CPC ............. G01N 33/49; G01N 35/00623; G01N 35/00871; G01N 21/6428; G01N 27/06; G01N 2021/6439; G01N 2035/00633; G01N 2035/00653
See application file for complete search history.

(56) References Cited

U.S. PATENT DOCUMENTS

| | | | |
|---|---|---|---|
| 6,525,807 B1 | 2/2003 | Morikawa et al. | |
| 8,968,653 B2 | 3/2015 | Fukuma et al. | |

(Continued)

FOREIGN PATENT DOCUMENTS

| | | |
|---|---|---|
| CN | 1834659 A | 9/2006 |
| CN | 101046435 A | 10/2007 |

(Continued)

OTHER PUBLICATIONS

Tanaka, Y. et al., "Performance Evaluation of Platelet Counting by Novel Fluorescent Dye Staining in the XN-Series Automated Hematology Analyzers", *Journal of Clinical Laboratory Analyzers*, 2014, pp. 1-8.

(Continued)

*Primary Examiner* — Benjamin R Whatley
(74) *Attorney, Agent, or Firm* — Brinks Gilson & Lione

(57) ABSTRACT

A method of controlling a blood analyzer for measuring platelets is provided. The method comprises: determining a relationship between at least one first measurement value obtained by detecting platelets in at least one previous test by an electrical type detector of the blood analyzer and at least one second measurement value obtained by detecting the platelets in the at least one previous test by an optical type detector of the blood analyzer, and controlling the blood analyzer to prepare the first and/or second measurement sample for a current test according to the determined relationship.

13 Claims, 15 Drawing Sheets

Fig. 14

(52) U.S. Cl.
CPC ........... *G01N 2015/1062* (2013.01); *G01N 2015/1486* (2013.01); *G01N 2021/6439* (2013.01); *G01N 2035/00633* (2013.01); *G01N 2035/00653* (2013.01)

(56) References Cited

U.S. PATENT DOCUMENTS

| | | | |
|---|---|---|---|
| 2006/0210438 A1 | 9/2006 | Nagai et al. | |
| 2007/0217951 A1 | 9/2007 | Matsumoto | |
| 2007/0231206 A1 | 10/2007 | Nagai et al. | |
| 2013/0065317 A1* | 3/2013 | Fukuma | G01N 15/12 436/63 |
| 2013/0262143 A1* | 10/2013 | Katou | G01N 35/00603 705/3 |

FOREIGN PATENT DOCUMENTS

| | | |
|---|---|---|
| CN | 102636635 A | 8/2012 |
| JP | 2000-275163 A | 10/2000 |
| JP | 2007-271348 A | 10/2007 |
| JP | 2010-107216 A | 5/2010 |
| JP | 2013-210267 A | 10/2013 |
| JP | 2015-010939 A | 1/2015 |
| WO | 2011/140042 A1 | 11/2011 |

OTHER PUBLICATIONS

The Chinese Office Action dated Jul. 2, 2019 in a counterpart Chinese patent application No. 201710228398.8.

The Chinese Office Action dated Jan. 17, 2020 in a counterpart Chinese patent application No. 201710228398.8.

Tina Dadu et al.: "Comparison of platelet counts by sysmex XE 2100 and LH-750 with the international flow reference method in thrombocytopenic patients", Indian Journal of Pathology and Microbiology, vol. 56, Issue No. 2, 2013, pp. 114-119, Internet<URL:https://www.ijpmonline.org/text.asp?2013/56/2/114/118701>, 4 pages; Cited in the Japanese Office Action dated Feb. 9, 2021 in a counterpart Japanese patent application.

Kazuto Tsuruda et al.: "Evaluation and Clinical Usefulness of the Automated Hematology Analyzer, Sysmex XE-2100 TM", Sysmex Journal International, vol. 9, No. 2, 1999, pp. 129-138; Cited in the Japanese Office Action dated Feb. 9, 2021 in a counterpart Japanese patent application.

Japanese Office Action dated Feb. 9, 2021 in a counterpart Japanese patent application No. 2017-114838.

Japanese Office Action dated Apr. 6, 2021 in a counterpart Japanese patent application No. 2017-114838.

* cited by examiner

| | PREVIOUS DETECTION TIMES | | PLT-I MEASUREMENT VALUE | PLT-F MEASUREMENT VALUE |
|---|---|---|---|---|
| PATIENT 1 | 02/05/2016 | 10:00AM | VALUE | — |
| | 03/05/2016 | 11:00AM | VALUE | — |
| | 04/05/2016 | 9:15AM | VALUE | VALUE |
| PATIENT 2 | 01/05/2016 | 3:00PM | VALUE | — |
| | 02/05/2016 | 3:15AM | VALUE | VALUE |
| | 03/05/2016 | 2:30AM | VALUE | VALUE |
| | 04/05/2016 | 10:00AM | VALUE | VALUE |
| PATIENT 3 | 01/05/2016 | 3:00PM | VALUE | — |
| | 02/05/2016 | 3:15AM | VALUE | VALUE |
| | 03/05/2016 | 2:30AM | VALUE | VALUE |
| | 04/05/2016 | 10:00AM | VALUE | VALUE |
| | 05/05/2016 | 3:00PM | VALUE | — |

Fig. 12

METHOD OF CONTROLLING A BLOOD ANALYZER FOR MEASURING PLATELETS

CROSS REFERENCE TO RELATED APPLICATIONS

This application claims priority from prior European Patent Application No. 16174984.1, filed on Jun. 17, 2016, entitled "METHOD OF CONTROLLING A BLOOD ANALYZER FOR MEASURING PLATELETS", the entire content of which is incorporated herein by reference.

FIELD OF THE INVENTION

The present invention relates to a control method and a controller for a blood analyzer for measuring platelets, a corresponding blood analyzer, and a computer-readable storage medium which are for providing a consistent reliable analysis of platelets in a blood sample.

BACKGROUND

Many blood analyzers have been developed for measuring the size of predetermined component particles in a sample such as blood, urine and the like, and analyzing the state of the particle distributions. Particularly in blood analyzers for detecting the distribution states of red blood cells, white blood cells, platelets and the like, red blood cells and platelets are measured by using an electrical resistance type measuring device since platelets have a relatively small size of 1 to 4 μm compared to the size of red blood cells which are 7 to 8 μm.

However, small size red blood cells may exist. Also, collapsed red blood cells have smaller size than usual. In those cases, red blood cells and platelets cannot be reliably differentiated simply by the size.

Japanese Laid-Open Patent Publication No. 2000-275163 discloses a particle analyzer which produces highly reliable measurement results by measuring platelets by using both an electrical resistance type measuring device and an optical measuring device. This particle analyzer adopts more reliable platelet number between a platelet number by the electrical resistance type measuring device and a platelet number by the optical measuring device.

In the particle analyzer disclosed in Japanese Laid-Open Patent Publication No. 2000-275163, however, two types of measurement samples allocated from the same sample must be prepared, and the measurements are performed by the electrical resistance type measuring device (also referred to as an electrical type detector in the following) and the optical type measuring device using the respective measurement samples. Disadvantages thus arise relating to the cost of the reagents used in the preparations, and the simple doubling of the number of measurement processes, which make it difficult to reduce analysis costs.

SUMMARY OF THE INVENTION

Problems with Existing Solutions

For monitoring of platelet counts from the same patient obtained at different time points, it is, however, important to continuously provide platelet counts having the same level of accuracy, or in other words the same level of reliability. While it would be possible to continuously provide the platelet counts having the same level of accuracy (reliability) based on the technique described in EP 2 182 365 A2 and the platelets would then be measured by a highly accurate methodology such as fluorescent platelet counts (PLT-F) based on the optical type measuring device, such a more accurate (reliable) methodology necessitates higher analysis costs. The reason for the higher analysis costs are based on the fact that the fluorescent platelet count (PLT-F) methodology requires a stain solution for staining platelets, and the like. Therefore, it is desired to provide an accurate (reliable) control of the platelet counts measurements while preventing unnecessary additional costs.

Solution

Accordingly, it is an object of the present invention to solve the above-described problems. In particular, it is an object of the present invention to overcome the above-described limitations that result from the need to balance a consistent level of accuracy (reliability) with a reduction of analysis costs.

A suitable method of controlling a blood analyzer for measuring platelets, a controller of the blood analyzer, a blood analyzer, a computer-readable storage medium, and a computer program are defined in the independent claims. Advantageous embodiments are defined by the respective dependent claims. The scope of the present invention is defined solely by the appended claims, and is not affected to any degree by the statements within this summary.

A first aspect of the present invention is a method of controlling a blood analyzer for measuring platelets, comprising: determining a relationship between at least one first measurement value obtained by detecting platelets in a blood sample of a patient in at least one previous test by an electrical type detector of the blood analyzer and at least one second measurement value obtained by detecting platelets in a blood sample of the patient in the at least one previous test by an optical type detector of the blood analyzer, and controlling the blood analyzer to prepare, from a blood sample of the patient, a first measurement sample for the electrical type detector and/or a second measurement sample for the optical type detector for a current test according to the determined relationship.

According to the present embodiment, a proper methodology (electrical type method or optical type method) for detecting platelets in a blood sample of a patient may be selected based on the relationship between at least one first measurement value and at least one second measurement value from the same patient in the at least one previous test. For example, in case the difference of measurement values between electrical type method and optical type method from the previous sample is large and therefore the measurement value of electrical type method in the previous test is unreliable, the optical type method, which is more reliable than the electrical type method, can be selected for the current test without electrical type measurement. On the other hand, if previous measurement values of electrical type method and optical type method are similar and therefore the measurement value of electrical type method in the previous test is reliable, optical type measurement can be omitted and only the electrical type measurement can be performed for the current test in order to avoid unnecessary optical type measurement. This will lead to improved monitoring of platelet counts in a patient because comparable platelet counts are evaluated. In addition, unnecessary additional costs due to optical type measurements are prevented.

A second aspect of the present invention is a controller of a blood analyzer for measuring platelets, configured to perform operations comprising: determining a relationship between at least one first measurement value obtained by detecting platelets in a blood sample of a patient in at least one previous test by an electrical type detector of the blood analyzer and at least one second measurement value obtained by detecting platelets in a blood sample of the patient in the at least one previous test by an optical type detector of the blood analyzer, and controlling the blood analyzer to prepare, from a blood sample of the patient, a first measurement sample for the electrical type detector and/or a second measurement sample for the optical type detector for a current test according to the determined relationship.

A third aspect of the present invention is a blood analyzer for measuring platelets, comprising a sample preparing section configured to prepare a first measurement sample for measurement of platelets by an electrical measuring method and configured to prepare a second measurement sample for measurement of platelets by an optical measuring method; an electrical type detector configured to detect platelets in the first measurement sample prepared by the sample preparing section; an optical type detector configured to detect platelets in the second measurement sample prepared by the sample preparing section; and a controller according to the second aspect of the present invention.

BRIEF DESCRIPTION OF THE DRAWINGS

The embodiments herein will now be further described in more detail in the following detailed description by reference to the appended drawings illustrating the embodiments and in which:

FIG. 12 shows a patient-specific detection history according to the embodiment of the present invention.

DETAILED DESCRIPTION OF THE PREFERRED EMBODIMENTS

In the following, embodiments are described with reference to the appended Figures. It is noted that the following description contains examples only and should not be construed as limiting the invention. A person skilled in the art will recognize additional features and advantages upon reading the following detailed description. Further, similar or same reference signs indicate similar or same elements or operations. The embodiments are described in detail below by way of example of a blood analyzer for analyzing blood used as a blood analyzer with reference to the drawings.

Figure 1:
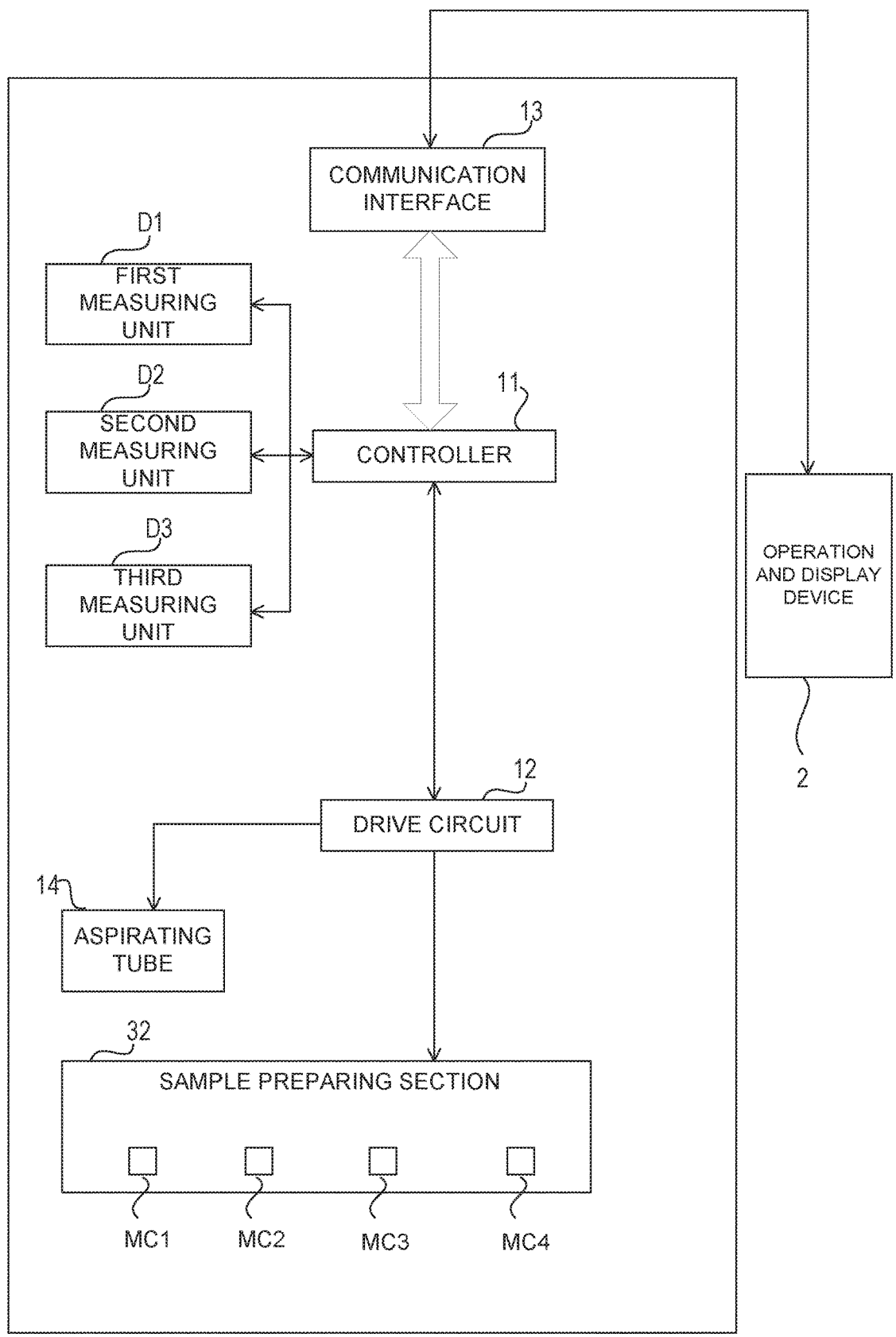
FIG. 1 is a block diagram showing the structure of an embodiment of the blood analyzer of the present invention.

FIG. 1 is a block diagram showing the structure of an embodiment of the blood analyzer of the present invention. The blood analyzer of the embodiment of the present invention is configured by connecting an analyzer body 1 and an operation and display device 2 so as to be capable of data communication. The operation and display device 2 (also referred to as Information Processing Unit: IPU) has sample analysis software installed for various types of setting related to analysis, displaying analysis results and the like; instructions are transmitted to the analyzer body 1 and measurement data are received from the analyzer body 1 via data communication between the analyzer body 1 and the operation and display device 2. The analyzer body 1 is provided with an aspirating tube 14, a sample preparing section 32, first to third measuring units D1, D2, D3. The aspirating tube 14 aspirates a blood sample from a collection tube 3 which is described later. The sample preparing section 32 includes first to fourth mixing chambers MC1, MC2, MC3, MC4 and prepares various measurement samples by mixing the aspirated blood sample and reagents within the chambers MC1, MC2, MC3, MC4. The analyzer body 1 is provided with a controller 11 for controlling the operations of the sample preparing section 32, the first to third measuring units D1, D2, D3. The controller 11 is capable of data communication with the operation and display device 2, so as to send and receive various types of signals and data to/from the operation and display device 2 through a communication interface 13. The analyzer body 1 is also provided with a drive circuit 12 for operating the aspirating tube 14 and the sample preparing section 32.

Figure 2:
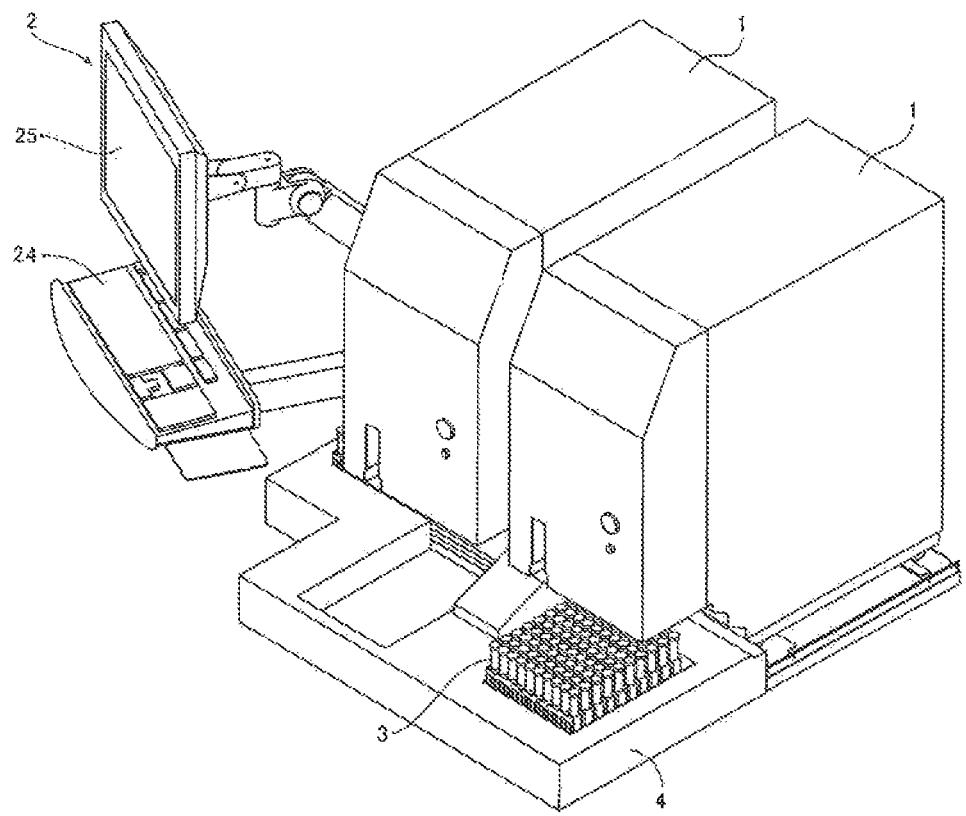
FIG. 2 is a perspective view showing the external structure of the blood analyzer of the embodiment of the present invention.
Figure 3:
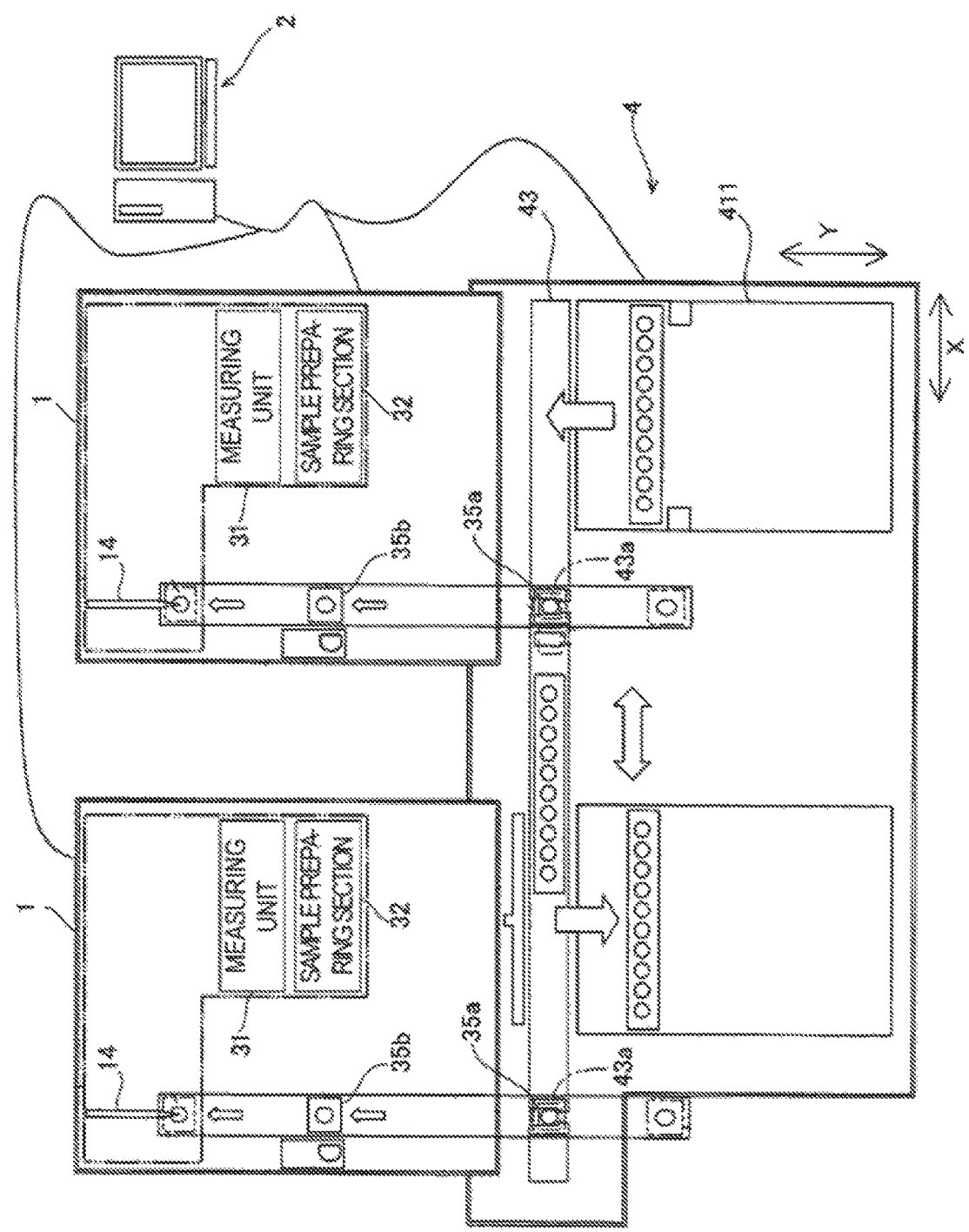
FIG. 3 is a top view showing the internal structure of the body of the embodiment of the blood analyzer of the present invention.

FIG. 2 is a perspective view showing the external structure of the blood analyzer of the embodiment of the present invention, and FIG. 3 is a top view showing the internal structure of the analyzer body 1 of the embodiment of the present invention. The analyzer body 1 is a blood analyzer for analyzing (measuring analyzing and the like) blood (sample) contained in a sealed container (initial container of a measurement sample) collection tube 3, and is provided with a sample transport section 4 for transporting the collection tube 3 to a predetermined position at which the analyzer body 1 obtains the sample. The blood analyzer includes two analyzer bodies 1, each having the same structure. The analyzer body 1 includes the sample preparing section 32 and a measuring unit 31 which has the measuring units D1, D2, D3.

The aspirating tube (aspirator) 14 pierces a cap sealing the interior of the collection tube 3 and aspirating the sample within the collection tube 3, which is transported to an aspiration position for aspirating a blood sample from the collection tube 3. A sample rack holding multiple collection tubes 3 is set by a user on a rack placement section 411 and is transported into a transport path 43. The transport path 43 transports the sample rack to a grasping position 35a for grasping a collection tube 3 by a catcher 43a. The collection tube 3 is moved by the catcher 43a into a tube holder 35b from the sample rack, and the collection tube 3 is transported by the tube holder 35b to the aspiration position. The sample preparing section 32 prepares measurement samples for various analyses by mixing a predetermined amount of blood aspirated from the collection tube 3 with reagent within a first mixing chamber (first container: HGB/RBC chamber) MC1, second mixing chamber (second container: WBC chamber) MC2, third mixing chamber (third container: RET chamber) MC3, or fourth mixing chamber (fourth container: PLT chamber) MC4.

The sample preparing section 32 prepares a RBC/PLT measurement sample for electrically measuring red blood cells (RBC) and platelets (PLT) by mixing a blood sample and a dilution liquid within the first mixing chamber MC1. A part of the prepared RBC/PLT measurement sample is measured by the first measuring unit D1. The sample preparing section 32 further prepares a HGB measurement sample for a measurement of hemoglobin (HGB) by adding a hemoglobin hemolytic agent to other part of the RBC/PLT measurement sample left within the first mixing chamber MC1. The HGB measurement sample is measured by the second measuring unit D2.

The sample preparing section 32 prepares a WBC measurement sample for classifying white blood cells into sub-groups by mixing a blood sample, a white blood cell classifying hemolytic agent and a white blood cell classifying stain within the second mixing chamber MC2. The WBC measurement sample is measured by the third measuring unit D3. The sample preparing section 32 prepares a RET measurement sample for measuring reticulocytes (RET) by mixing a blood sample, a reticulocyte stain and a reticulocyte diluting liquid within the third mixing chamber MC3. The RET measurement sample is measured by the third measuring unit D3.

The sample preparing section 32 prepares a PLT measurement sample for optically measuring platelets by mixing a blood sample, a platelet stain and a platelet diluting liquid. The PLT measurement sample is measured by the third measuring unit D3. As the platelet stain, for example, Nile Blue may be used. The platelet stain includes Nile Blue Hydrogen sulfate as a staining dye, which comprises a compound of the following formula:

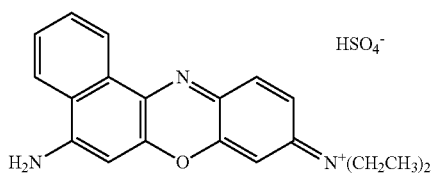

Further details of this compound are described in EP 2 273 264 A1.

The first measuring unit (first detector, i.e. an electrical type detector) D1 performs measurements relating to red blood cells and platelets, and the second measuring unit D2 performs measurements relating to hemoglobin. The third measuring unit (second detector, i.e. optical type detector) D3 performs measurements relating to white blood cells. The first mixing chamber MC1 is a part for preparing a measurement sample for analyses relating to red blood cells, platelets, and hemoglobin; the measurement sample prepared by the first mixing chamber MC1 is used in measurements performed by the first measuring unit D1 and second measuring unit D2. The second mixing chamber MC2 is a part for preparing a measurement sample for analyses relating to white blood cells; the measurement sample prepared by the second mixing chamber MC2 is used in measurements performed by the third measuring unit D3.

The first measuring unit D1 is configured as an RBC/PLT detector for performing RBC measurements (measuring red blood cell count), and PLT measurements (measuring platelet count). The first measuring unit D1 can perform RBC and PLT measurements via a sheath flow DC detection method, and is a so-called electrical resistance measuring device. For the PLT measurements according to the electrical resistance measurement method, this is also referred to as PLT-I in the following.

The second measuring unit D2 is configured as an HGB detector for performing HGB measurements (measuring the amount of pigment in the blood). The second measuring unit D2 can perform HGB measurements via an SLS-hemoglobin method.

The third measuring unit D3 is configured as an optical detector capable of performing WBC measurements (white blood cell count), RET measurements (reticulocyte count), and PLT measurements (platelet count). The third measuring unit D3 performs WBC measurements, RET measurements, and PLT measurements by flow cytometry using a semiconductor laser, and is a so-called optical type measuring device. For the PLT measurements according to the optical measurement method, this is also referred to as PLT-F in the following.

Figure 4:
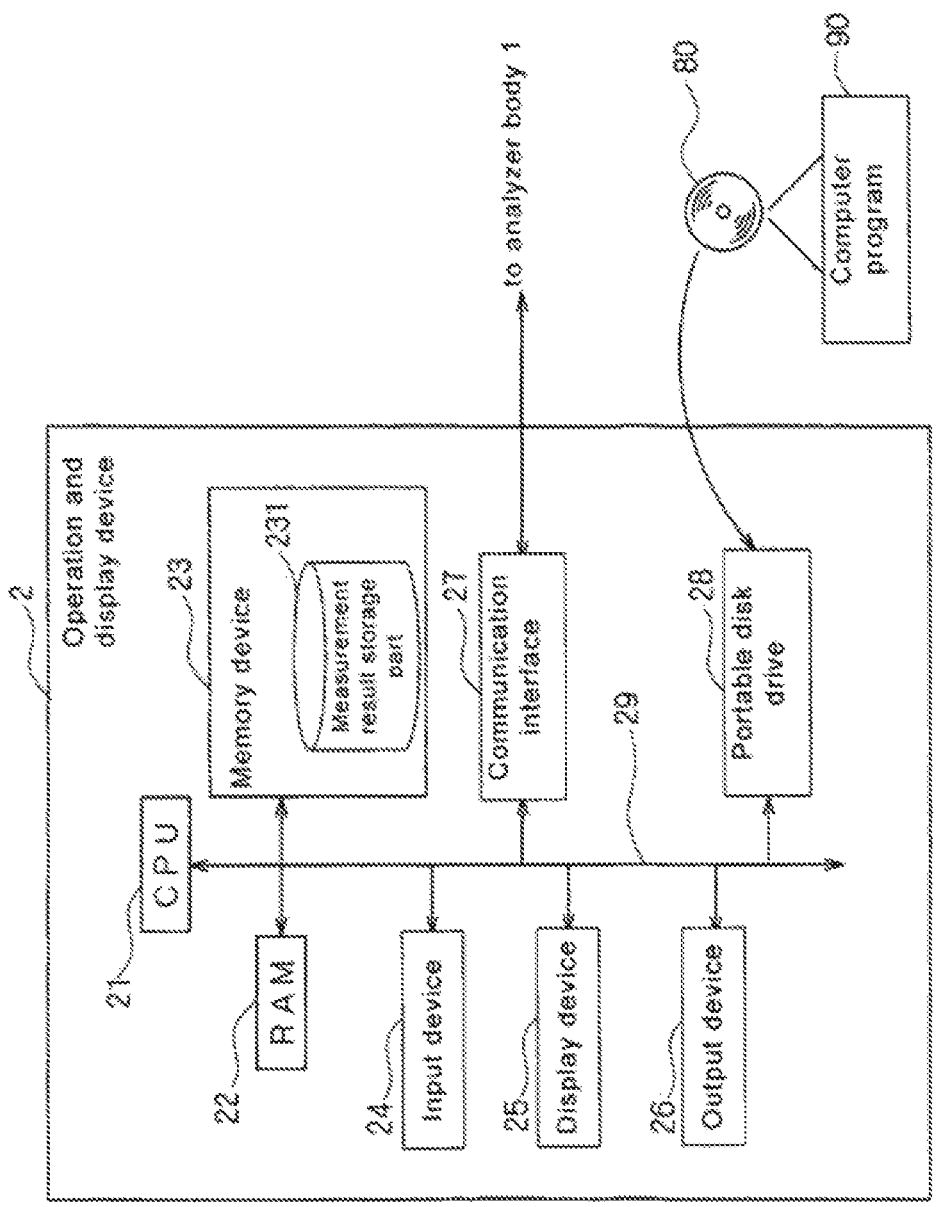
FIG. 4 is a block diagram showing the structure of an embodiment of the operation and display device of the present invention.

FIG. 4 is a block diagram showing the structure of an embodiment of the operation and display device of the present invention. As shown in FIG. 4, the operation and display device 2 is configured by a CPU (central processing unit) 21, RAM 22, memory device 23, input device 24, display device 25, output device 26, communication interface 27, portable disk drive 28, and an internal bus 29 connecting all the above-mentioned hardware. The CPU 21 is connected to the various hardware of the operation and display device 2 mentioned above via the internal bus 29, and controls these various hardware components and performs various software functions according to a computer program 90 stored on the memory device 23. The RAM 22 is configured by a volatile memory such as an SRAM, SDRAM or the like, and is used for developing modules during the execution of the computer program 90, and for temporarily storing data generated during the execution of the computer program 90. It is noted that the operation and display device 2 may also be constituted by a plurality of interconnected devices having a plurality of interconnected CPUs, a plurality of interconnected memory devices, and the like.

The memory device 23 may be configured by a built-in fixed type memory device (hard disk), volatile memory such as an SRAM, or nonvolatile memory such as a ROM. The computer program 90 stored on the memory device 23 may be downloaded from a portable memory medium 80 such as a DVD, CD-ROM or the like which stores information such as programs and data via the portable disk drive 28, and developed from the memory device 23 to the RAM 22 during execution. Of course, the computer program 90 may also be downloaded from an external computer connected via the communication interface 27.

The memory device 23 is provided with a measurement result storage part 231 for storing the measurement results of the first measuring unit D1, second measuring unit D2, and third measuring unit D3; the CPU 21 determines the reliability of the detection results based on the stored measurement results.

The communication interface is connected to the internal bus 29, and is capable of sending and receiving data via a communication line connected to the analyzer body 1. That is, instruction information to start a measurement can be sent to the analyzer body 1 and measurement data such as measurement results and the like can be received.

The input device 24 is a data input medium such as a keyboard and mouse or the like. The display device 25 is a CRT monitor, LCD or similar display device for graphically displaying analysis results. The output device 26 is a printing device such as a laser printer, inkjet printer or the like.

The analyzer body 1 has two measurement modes relating to the measurement of platelets in the blood. The first measurement mode is the complete blood count (CBC) measurement mode in which RBC measurements and PLT measurements are performed by the first measuring unit D1, and WBC measurements are performed by the third measuring unit D3. The second measurement mode is the CBC+PLT-F measurement mode in which RBC measurements and PLT measurements are performed by the first measuring unit D1, and the WBC measurements and PLT measurements are performed by the third measuring unit D3. That is, the PLT measurements may be performed by both the electrical resistance type measuring device (PLT-I) and the optical type measuring device (also used for PLT-F in CBC+PLT-F measurement mode).

The operation of the blood analyzer is described below when the CBC measurement mode (first measurement mode) has been selected in the embodiment. In the analyzer body 1 of the embodiment, when the CBC measurement mode has been selected, the RBC measurement and PLT measurement is performed by the first measuring device (detector, first detector) D1 which is an electrical resistance type measuring device (PLT-I), and the WBC measurements are performed by the third measuring unit (other detector, second detector) D3 which is an optical type measuring device (PLT-F).

Figure 5:
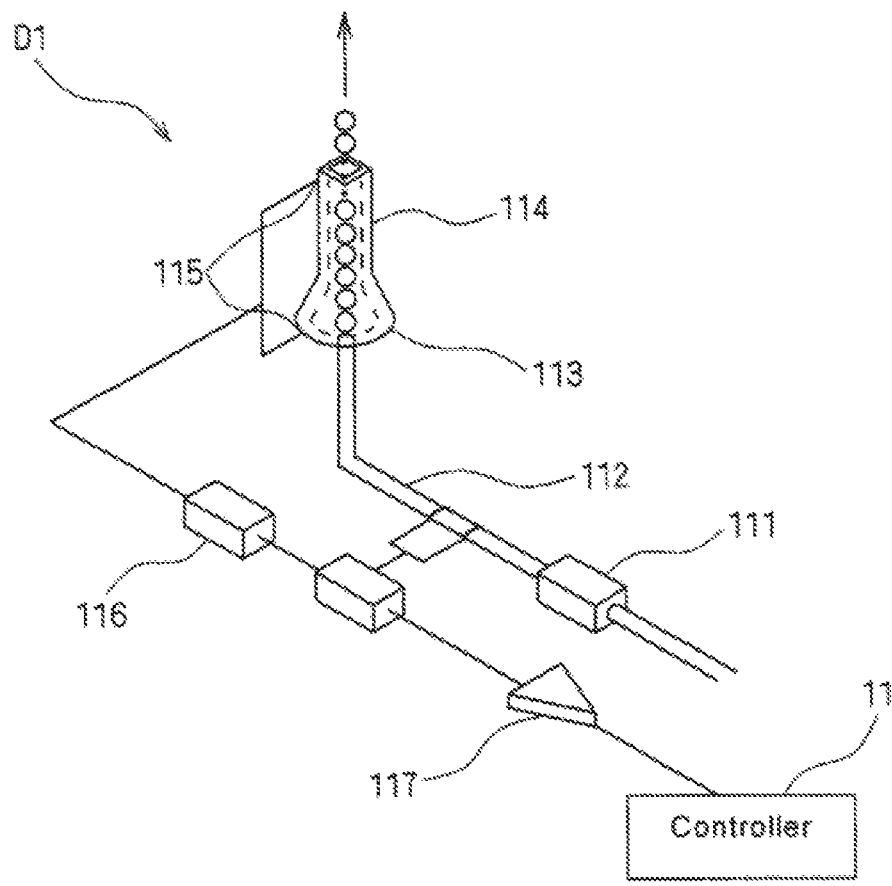
FIG. 5 is a schematic view showing the main structure of a first measuring device, which is an electrical resistance type measuring device according to the embodiment of the present invention.

FIG. 5 is a schematic view showing the main structure of a first measuring unit D1, which is an electrical resistance type measuring device (PLT-I). The first measuring unit D1 has a reactor 111; the blood sample aspirated by the aspirating tube 14, and introduced together with diluting liquid into the reactor 111.

A flow channel 112 extends from the reactor 111, and a sheath flow cell 113 is provided at the end of the flow channel 112. The measurement sample diluted in the reactor 111 is delivered to the sheath flow cell 113 through the flow channel 112. The first measuring unit D1 is provided with a sheath liquid chamber that is not shown in the drawing, so that the sheath fluid stored in the sheath fluid chamber can be supplied to the sheath flow cell 113.

In the sheath flow cell 113, a flow is formed in which the measurement sample is encapsulated by the sheath fluid. The sheath flow cell 113 is provided with an orifice 114, the flow of the measurement sample is constricted by the orifice 114 so that the particles (tangible material) contained in the measurement sample pass one by one through the orifice 114. The sheath flow cell 113 is provided with a pair of electrodes 115 which are disposed so as to have the orifice 114 interposed in between. A direct current (DC) power source 116 is connected to the pair of electrodes 115 to supply a DC current between the pair of electrodes 115. Then, the impedance is detected between the pair of electrodes 115 while the DC current is supplied from the DC power source 116.

The electrical resistance signals representing the change in impedance are amplified by an amp 117 and transmitted to the controller 11. The magnitude of the electrical resistance signal corresponds to the volume (size) of the particle; thus the volume of the particle can be obtained when the controller 11 performs signal processing of the electrical resistance signal.

Figure 6:
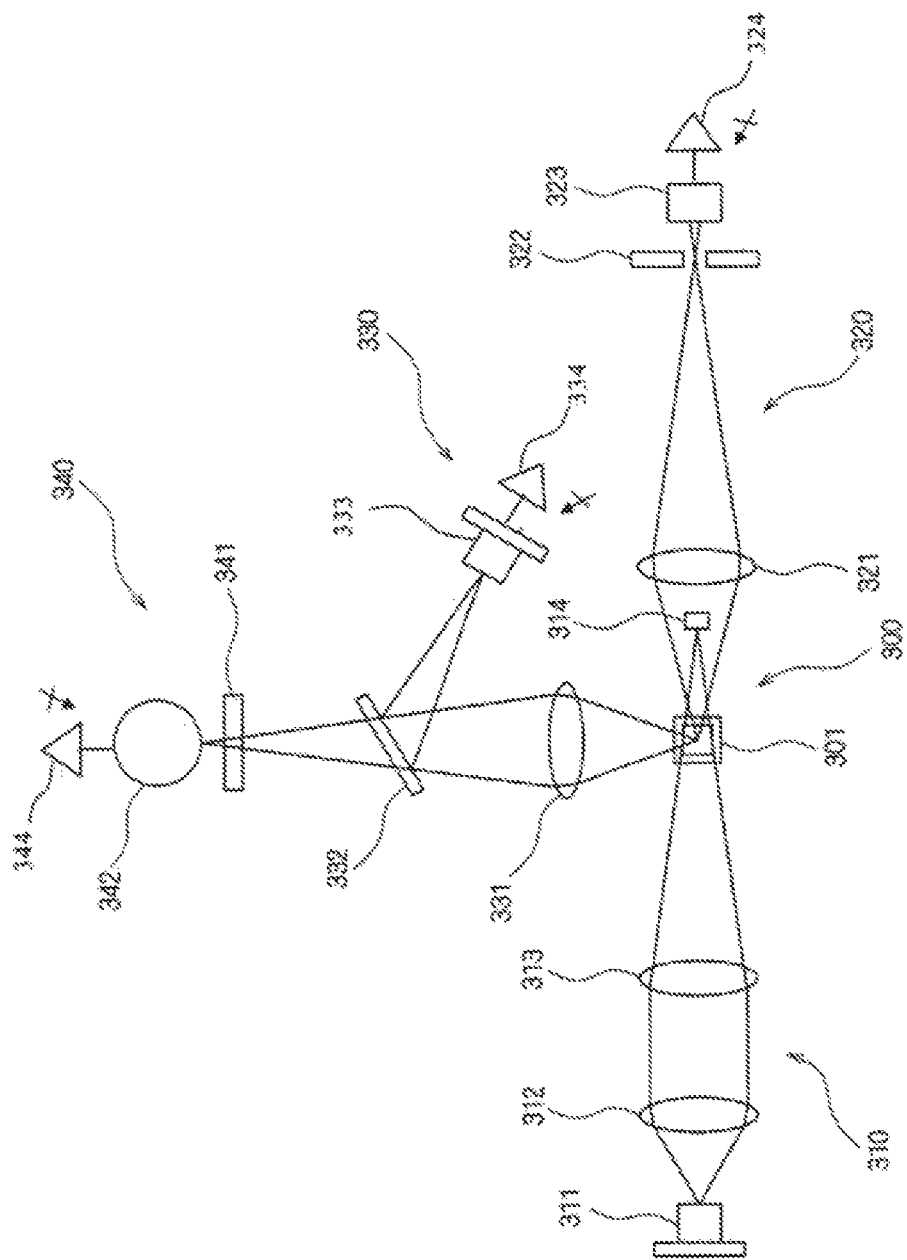
FIG. 6 is a schematic view showing the main structure of a third measuring device, which is an optical type measuring device according to the embodiment of the present invention.

FIG. 6 is a schematic view showing the structure of the third measuring unit D3, which is an optical type measuring device (PLT-I). The third measuring unit D3 receives the measurement sample at a flow cell 301, a flow is formed in the flow cell 301, the blood cells contained in the flow passing within the flow cell 301 are irradiated by a semiconductor laser light, and the blood cells are measured. The third measuring unit D3 has a sheath flow system 300, beam spot system 310, forward scattered light receiving system 320, side scattered light receiving system 330, and side fluorescent light receiving system 340.

The sheath flow system 300 forms a flow in which the blood cells contained in the measurement sample are aligned in a single row within the flow cell 301, thus improving the accuracy and reproducibility of the blood cell count. The beam spot system 310 is configured so that light emitted from the semiconductor laser 311 passes through a collimator lens 312 and condenser lens 313, and irradiates the flow cell 301. The beam spot system 310 is also provided with a beam stopper 314.

The forward scattered light receiving system 320 is configured so that the forward scattered light is collected by a forward collector lens 321, and the light passing through a pinhole 322 is received by a forward scattered light receiver (photodiode) 323, and the signal output from the forward scattered light receiver 323 according to the amount of received light is amplified by an amplifier 324. The amplification factor of the amplifier 324 is set by the CPU 21.

The side scattered light receiving system 330 is configured so that the side scattered light is collected by a side scattered light collector lens 331, and part of the light is reflected by a dichroic mirror 332, received by a side scattered light receiver (photodiode) 333, and the signal output from the side scattered light receiver 333 according to the amount of received light is amplified by an amplifier 334. The amplification factor of the amplifier 334 is set by the CPU 21.

The scattered light is a phenomenon which occurs due to the change in the direction of travel of the light caused by the presence of an obstacle in the direction in which the light is traveling, that is, a particle, such as a blood cell. Information relating to the size and material quality of the particle can be obtained by detecting the scattered light. Particularly information relating to the size of the particle (blood cell) can be obtained from the forward scattered light. Information relating to the interior of the particle, such as information concerning the material quality of the particle, can be obtained from the side scattered light.

The side fluorescent light receiving system 340 is configured so that the light passing through the dichroic mirror 332 then passes through a spectral filter 341 and is received by a fluorescent light receiver (photomultiplier) 342, and the signal output from the fluorescent light receiver 342 according to the amount of received light is amplified by an amplifier 344. The amplification factor of the amplifier 344 is set by the CPU 21.

When a fluorescent material such as a stained blood cell is irradiated with light, the fluorescent material generates light that has a longer wavelength than the irradiating light. The fluorescent intensity becomes stronger under heavy staining, so that information relating to the degree of staining of the blood cell can be obtained by measuring the intensity of the fluorescent light. Other measurements such as the classification of the blood cell can be performed via the differences in the side fluorescent light intensity.

When light is received by the light receivers 323, 333, and 342, the light receivers 323, 333, and 342 output electrical pulse signals, and measurement data are generated based on the output electrical pulse signals. The measurement data are transmitted from the analyzer body 1 to the operation and display device 2, and undergo processing and analysis in the operation and display device 2.

When the CBC measurement mode has been selected, the operation and display device 2 counts the platelets by particle size analysis of the platelets based on the measurement data of the first measuring unit D1. More specifically, the platelet count is analyzed by a histogram in which the platelet volume (units: fL) is plotted on the horizontal axis, and the number of platelets is plotted on the vertical axis.

Based on the above configuration of the blood analyzer, the following conventional operation has been performed with regard to PLT measurements:

The PLT measurement is performed by the first measuring unit D1 (PLT-I) in the blood analyzer having the above configuration. When, for example, small or fragmented red blood cells contaminate the sample and the size of the particles is measured by the first measuring unit D1, it becomes difficult to accurately count the platelets because these small or fragmented red blood cells may also be counted as platelets. In the blood analyzer of the embodiment of the present invention, when the measurement data of a first PLT measurement is analyzed and it is determined that the measurement data are not reliable, the PLT measurement is then performed by the third measuring unit D3 (PLT-F).

Figure 7:
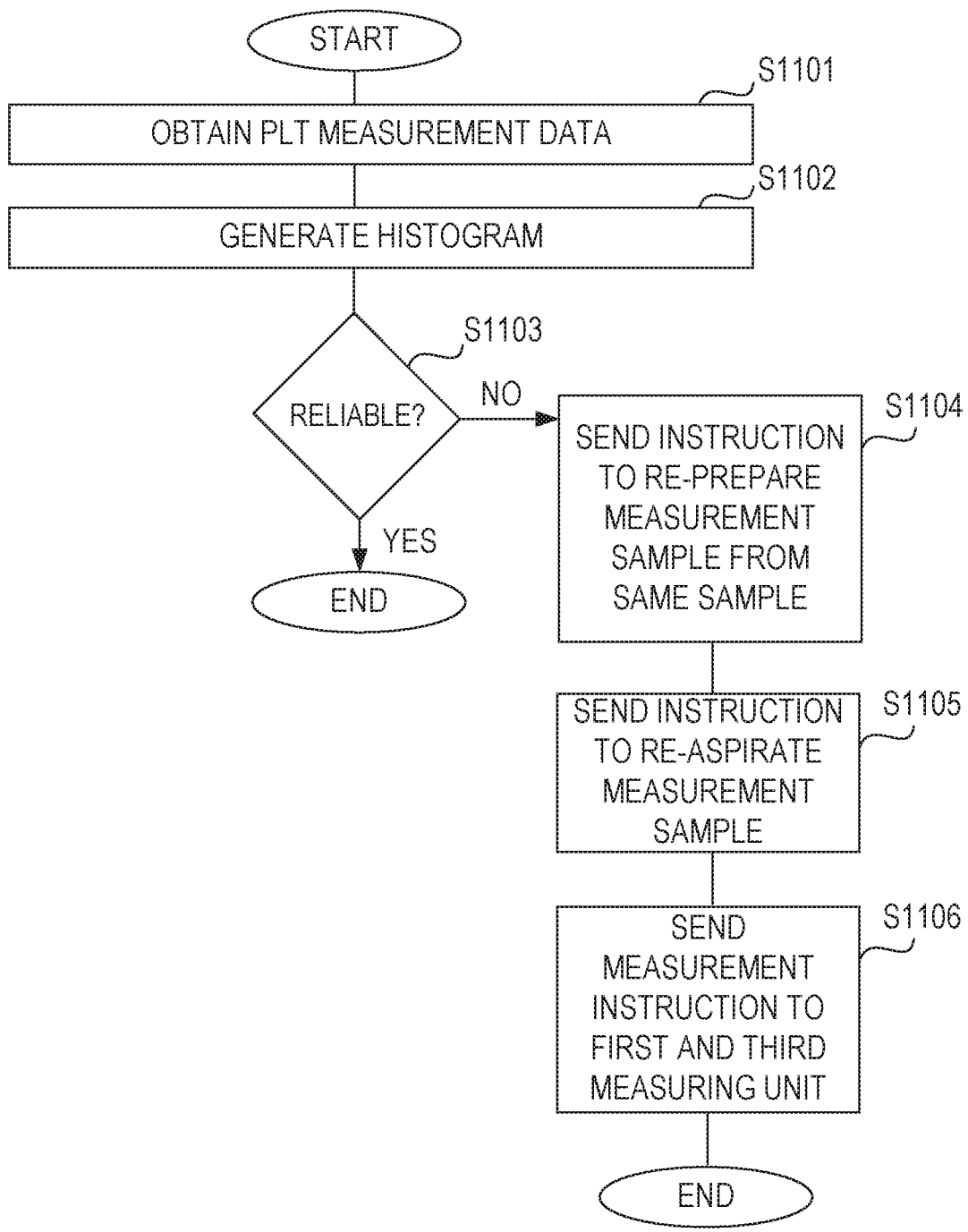
FIG. 7 is a flow chart showing the sequence of CPU processing of the operation and display device of the embodiment of the blood analyzer of the present invention.

FIG. 7 is a flow chart showing the sequence of the processing by the CPU 21 of the operation and display device 2 of the embodiment of the blood analyzer of the present invention. The CPU 21 of the operation and display device 2 obtains measurement data as a PLT measurement result from the controller 11 of the analyzer body 1 (step S1101).

The CPU 21 generates a histogram based on the obtained measurement data (step S1102), and displays the histogram on the display device 25. The generated histogram plots the platelet volume on the horizontal axis and the PLT count on the vertical axis.

The CPU 21 determines whether the measurement data are reliable (step S1103). The process of determining whether the PLT measurement data are reliable is not particularly limited. In the present embodiment, the measurement data are determined unreliable when the PLT count, that is, the number of platelets, is less than a predetermined value, or a platelet distribution anomaly occurs.

Figure 8:
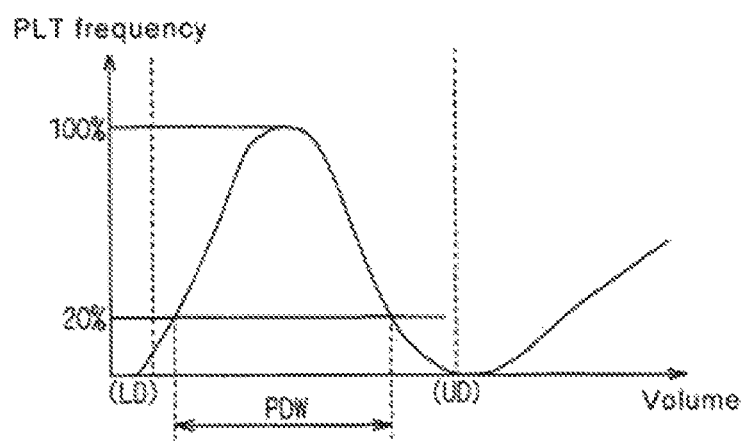
FIG. 8 shows an illustration of the reliability determination based on a histogram.

FIG. 8 shows an illustration of the reliability determination based on a histogram. The histogram of FIG. 8 shows the PLT count (count values) plotted on the vertical axis and the platelet size plotted on the horizontal axis. LD is the platelet size where a frequency standard for a predetermined small size is set; UD is the platelet size where a frequency standard for a predetermined large size is set. That is, when the PLT count exceeds the frequency standard at LD, the measurement data are determined to be unreliable due to the high possibility of impurities affecting the count. When the PLT count exceeds the frequency standard at UD, the measurement data are determined to be unreliable due to inadequate convergence, that is, the high possibility of impurities. In a normal situation, the count value is down gradually toward UD and converges at UD in the histogram.

The distribution width PDW is calculated for the 20% level when the height of the peak of the PLT count is 100%, and a distribution anomaly is determined to exist when PDW is greater than a predetermined standard width.

Figure 9A:
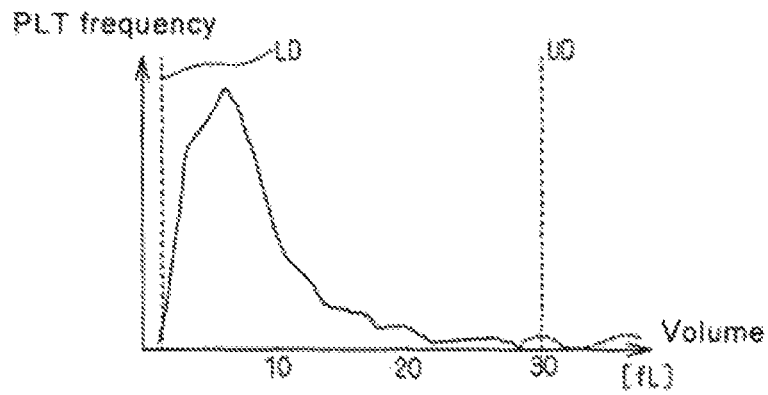
FIGS. 9A, 9B and 9C show an illustration of a histogram based on PLT measurement data.

FIG. 9 shows an illustration of a histogram based on PLT measurement data. FIG. 9A shows a pattern example of a measurement data histogram. As shown in FIG. 9A, when the measurement data are reliable, the PLT count in LD and UD are adequately smaller than the frequency standard, And the distribution width PDW is also smaller than the standard width.

Figure 9B:
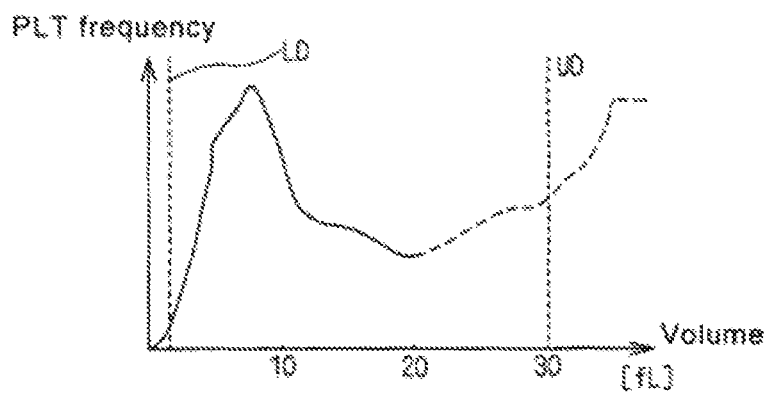

FIG. 9B shows an example of a histogram when the UD platelet count value exceeds the frequency standard. In this case, the UD PLT frequency exceeds the frequency standard, and the distribution width PDW does exceed the standard width, so a platelet distribution anomaly is determined.

Figure 9C:
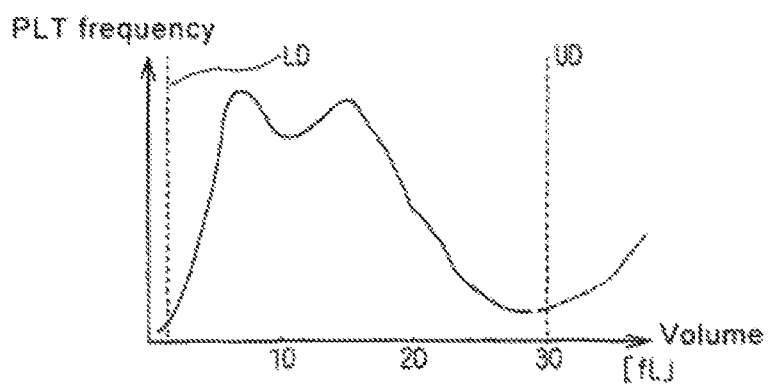

FIG. 9C shows an example of a histogram when there are two or more peaks in the PLT frequency. In this case, the LD and UD PLT frequency is adequately smaller than the frequency standard, but the distribution width PDW exceeds the predetermined standard width, so a platelet distribution anomaly is determined. A distribution anomaly may also be determined when there are two or more distribution peaks even though the distribution width PDW does not exceed the predetermined standard width.

Figure 10:
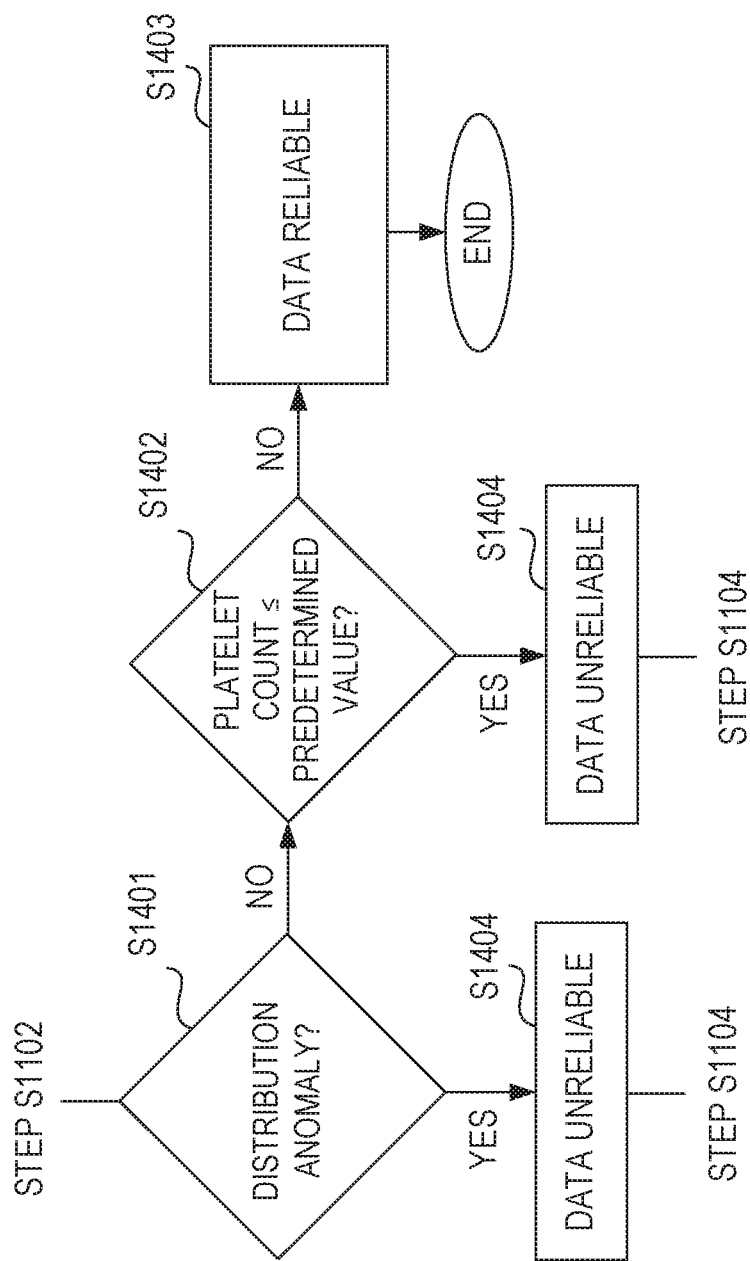
FIG. 10 is a flow chart showing the sequence of the reliability determination process of the operation and display device of the embodiment of the blood analyzer of the present invention.

FIG. 10 is a flow chart showing the sequence of the reliability determination process of the CPU 21 of the operation and display device 2 of the embodiment of the blood analyzer of the present invention. The CPU 21 of the operation and display device 2 generates a histogram based on the obtained measurement data (step S1102), and determines whether a platelet distribution anomaly exists (step S1401).

When the CPU 21 has determined that a platelet distribution anomaly exists (step S1401: YES), the CPU 21 then determines the data are unreliable (step S1404), and the process continues to step S1104. When the CPU 21 has determined that a platelet distribution anomaly does not exist (step S1401: NO), the CPU 21 then determines whether the platelet count value is less than a predetermined value (step S1402).

When the CPU 21 has determined that the platelet count value is less than the predetermined value (step S1402: YES), the CPU 21 then determines the data are unreliable (step S1404), and the process continues to step S1104. The reason for marking low counts as unreliable is that the imprecision gets bigger as counts get lower. When the CPU 21 has determined that the platelet count value exceeds a predetermined value (step S1402: NO), the CPU 21 determines the data are reliable (step S1403) and the process ends.

Returning now to FIG. 7, when the CPU 21 of the operation and display device 2 has determined that the data are unreliable (step S1103: NO) according to the processing as described above with regard to FIG. 10, the CPU 21 sends an instruction to again prepare a measurement sample from the same sample to the analyzer body 1 (step S1104). The controller 11 of the analyzer body 1 receives the re-preparation instruction, and issues an instruction to the drive circuit 12 to operate the sample preparing section 32.

The CPU 21 sends an instruction to re-aspirate the re-prepared measurement sample to the analyzer body 1 (step S1105). The controller 11 of the analyzer body 1 receives the re-aspiration instruction, and issues an instruction to the drive circuit 12 to operate the aspirating tube 14.

The CPU 21 sends a measurement instruction to measure the re-aspirated measurement sample by the first measuring unit D1 and by the third measuring unit D3, that is, to perform measurement using the electrical type measuring device and the optical type measuring device, respectively, to the analyzer body 1 (step S1106). The controller 11 of the analyzer body 1 receives the measurement instruction and sends a measurement start signal to the third measuring unit D3 (PLT-F) and the first measuring unit D1 (PLT-I). The CPU 21 generates measurement values of PLT-I and PLT-F based on measurement data from the first and third measuring units D1, D3, and sends the generated measurement values of PLT-I and PLT-F to WAM (described later). When both of the measurement values of PLT-I and PLT-F are obtained, the measurement value of PLT-F is stored as a test result of platelets in each memory device of WAM and the operation and display device 2. When the CPU 21 determines that the data are reliable (step S1103: YES), the CPU 21 ends the process.

Figure 11:
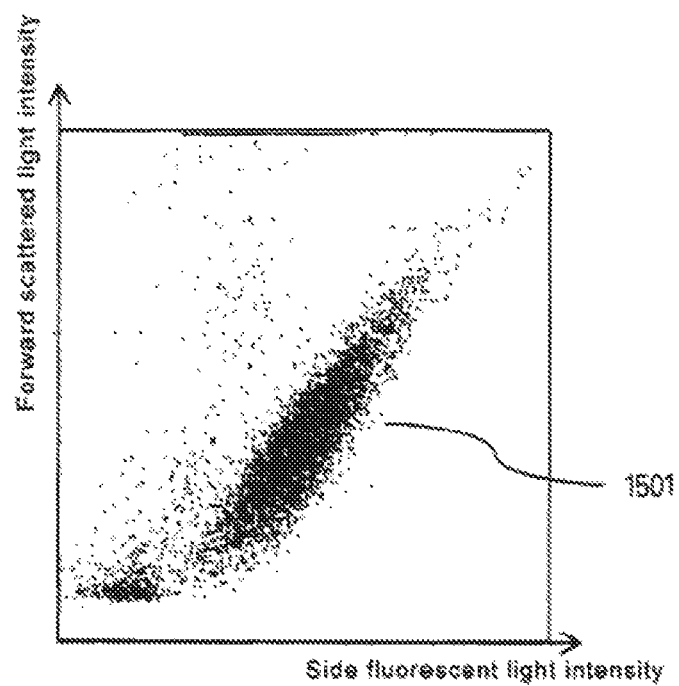
FIG. 11 shows an illustration of a scattergram representing the PLT re-measurement results of the embodiment of the blood analyzer of the present invention.

FIG. 11 shows an illustration of a scattergram representing the PLT re-measurement results of the embodiment of the blood analyzer of the present invention. In the scattergram of FIG. 11, the forward scattered light intensity is plotted on the vertical axis, and the side fluorescent light intensity is plotted on the horizontal axis; measurements are performed by using the dedicated stain (for example, Nile Blue) to increase the degree of staining of the platelets. As is made clear by FIG. 11, the platelet count value is concentrated in region 1501, and there is no region in which the red blood cells and impurities intersect. Therefore, the blood can be analyzed with excellent precision by changing the detection method of the embodiment, that is, the second detection condition according to the reliability of the first measurement data.

Since the measurement sample is re-prepared based on the same sample, and the operations of the sample preparing section and the aspirating tube 14 controlled so as to re-aspirate the prepared measurement sample only when reliable measurement data cannot be obtained as the detection results of the predetermined components, the reagent used in preparing the sample is conserved, and the increase in the number of measurement processes can be limited to a minimum.

The present embodiment, as explained above, is furthermore configured to control the sample preparing section to prepare, from a blood sample of a patient, the first measurement sample and/or the second measurement sample for a current detection time (the detection time is referred to in the following also as a test) according to a relationship between at least one first measurement value obtained by detecting the platelets in at least one previous test by the electrical type detector (first measuring unit D1, see above) and at least one second measurement value obtained by detecting the platelets in the at least one previous test by the optical type detector (third measuring unit D3, see above). The relationship indicates, as will be further detailed below, a reliability of the at least one first measurement value in the at least one previous test. In other words, this relationship indicates a measure of reliability of one (or more) previous measurement value(s) obtained by the electrical type detector based on a comparison with one (or more) previous measurement value(s) as obtained by the optical type detector. Based on this determined relationship, a decision is then made to control the preparation of a first and/or a second measurement sample.

In order to determine the above relationship a detection history of patients may be taken into account when making a decision whether to prepare the first measurement sample (for a subsequent usage of the first measurement unit D1 (PLT-I), i.e. electrical type detector) and/or whether to prepare the second measurement sample (for a subsequent usage of the third measurement unit D3 (PLT-F), i.e. the optical type detector). The usage of an appropriate measurement method is relevant, for example, in cases in which a platelet count should be observed over a specific time period (e.g., a plurality of days or weeks). Since the platelet counts that are actually detected by the first measurement unit D1 (PLT-I) and the third measurement unit D3 (PLT-F) may differ, an incorrect conclusion may be derived from the fact that the platelet count measured by PLT-I on a first day is compared with a platelet count measured by PLT-F on a second day, but such a comparison does not sufficiently distinguish between differences that are due to the intrinsic measurement reliabilities and differences that result from an actual change of the number of platelets in a patient between the first day and the second day. According to the embodiment, a decision as to the preparation of the appropriate measurement sample and the subsequent usage of the first detector (first measurement unit D1 (PLT-I), electrical type detector) and/or the second detector (third measurement unit D3 (PLT-F), optical type detector) is therefore based on a detection history of the patient which includes the one (or more) previous measurement value(s) obtained by the electrical type detector and the one (or more) previous measurement value(s) as obtained by the optical type detector for determining the relationship.

FIG. 12 illustrates a patient database that provides a detection history for respective patients. As may be taken from FIG. 12 the patient-specific detection history is provided for specific patients (patient 1, patient 2, . . . ) for which platelet counts have been detected previously. For example, the detection history for patient 1 indicates that 3 previous measurements have been conducted. In particular, the previous detection times (a previous detection time is also referred to as a previous test) may indicate both a specific date and time at which the previous measurements have been conducted. Furthermore, the patient-specific detection history indicates, based on a stored PLT-I detection value and/or a stored PLT-F detection value, whether the first detector (PLT-I) and/or the second detector (PLT-F) have been used for the at least one previous detection time. In the example of patient 1 according to the database illustrated in FIG. 12, it follows from the PLT-I measurement values that the first detector (PLT-I) has been used during all 3 previous detection times while it follows from the PLT-F measurement values that the second detector (PLT-F) has been used only for the last detection time (on Apr. 5, 2016). The patient-specific detection history thus includes specific measurement values as an indication that the respective detectors have been used.

Based on the thus provided and maintained patient-specific detection history, the embodiment may thus control the blood analyzer so that the preparation of the appropriate measurement sample(s) and the subsequent usage of the first detector (PLT-I) and/or the second detector (PLT-F) for detecting the platelets for a current detection time (also referred to as a current test) is based on the relationship between one (or more) previous measurement values obtained by the first and second detector. The one (or more) previous measurement values may be retrieved from the patient-specific detection history which indicates, as illustrated above, the detector usage and detection results for the platelets in at least one previous detection time.

Figure 13:
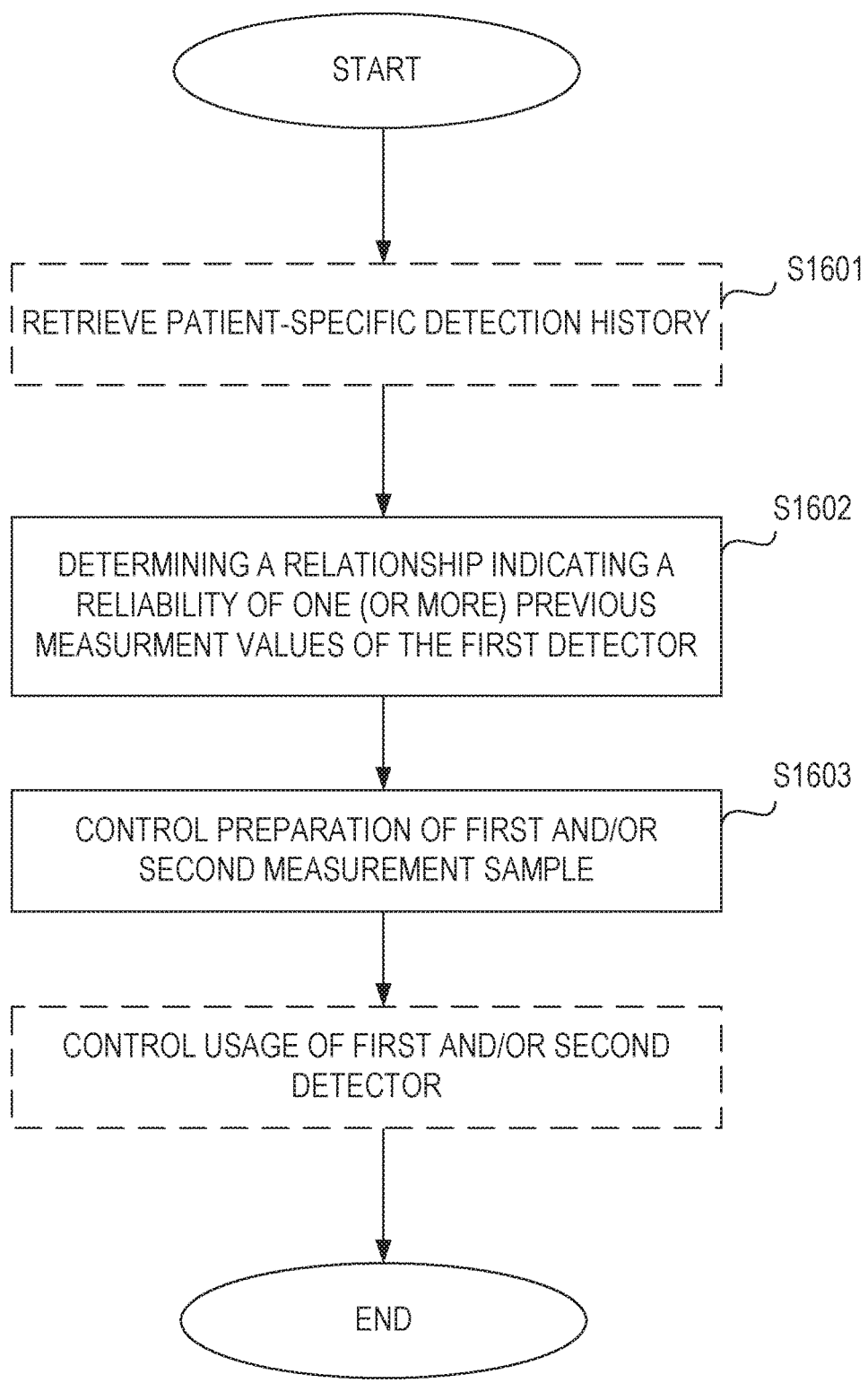
FIG. 13 is another flow chart showing the sequence of a method of controlling the blood analyzer according to the embodiment of the present invention.

FIG. 13 illustrates a method for controlling the blood analyzer according to the embodiment. Here, according to a first step S1601 a patient-specific detection history is retrieved from a database. Based on an evaluation of the patient-specific detection history, in particular with regard to which of the first (PLT-I) and/or second (PLT-F) detector has been used during a previous measurement time for detecting the platelet count for a specific patient, a decision may be made as to which detectors(s) should be used at a current detection time. For example, if only the first detector (PLT-I) had been used in the previous measurement time (test), then the first detector (PLT-I) should be used for the current measurement time. If both the first detector (PLT-I) and the second detector (PLT-F) had been used in one or more of the previous measurement time(s) (test(s)), then a relationship is determined between the measurement results of these previous tests.

The relationship may, for example, define a criterion to determine whether a difference that is defined based on the first measurement value previously obtained by the first detector and on the second measurement value previously obtained by the second detector is smaller than a predetermined value and thus warrants a measurement using the first detector for the current detection time.

Such a criterion may be further set not only on the basis of the last previous measurement values (i.e. last previous sample of the same patient) but also include additional measurement values for that patient, for example based on the second last, third last measurement values. As such, the relationship/criterion preferably takes into account at least one first measurement value which is obtained by detecting the platelets (predetermined component) in the at least one previous detection time by the first detector and at least one second measurement value obtained by detecting the platelets in the at least one previous detection time by the second detector.

Non-limiting examples of such a relationship criterion may be considered as follows, whereby |Delta PLT-I/PLT-F| defines an absolute difference between the previous PLT-I value and the previous PLT-F value:

|Delta PLT-I/PLT-F|/previous PLT-F>30% OR |Delta PLT-I/PLT-F|>15,000/µL for previous PLT-F between 0-80,000/µL

|Delta PLT-I/PLT-F|/previous PLT-F>20% OR |Delta PLT-I/PLT-F|>22,000/µL for previous PLT-F between 81,000-140,000/µL

||Delta PLT-I/PLT-F|/previous PLT-F>16% OR |Delta PLT-I/PLT-F|>27,000/µL for previous PLT-F between 141,000-200,000/µL

|Delta PLT-I/PLT-F|/previous PLT-F>14% OR |Delta PLT-I/PLT-F|>50,000/µL for previous PLT-F above 201,000/µL As may be taken from the above non-limiting examples, the relationship criterion may depend on the concentration of the platelets in the sample and thus advantageously takes into account that the accuracy/reliability levels of the two detection methodologies may differ as a function of the platelet concentration.

The relationship (criterion) may therefore indicate that the PLT-I measurement result by the first detector (PLT-I) has the same accuracy/reliability level as the detection result by the second detector (PLT-F). The present inventors have realized that such a relationship may be applied because detection results of the first detector (PLT-I) and the second detector (PLT-F) may approach each other at a later time point of a platelet count time series, even though in an earlier time point of such a platelet count time series the detection results differ significantly (see Tanaka et al., J Clin Lab Anal 2014; 28(5):341-348). In other words, in contrast to a conventional approach in which, once the PLT-F detector is used for measuring platelets, a next sample should be measured using the same methodology PLT-F for monitoring PLT counts accurately, according to the present embodiment, if a difference between the previous PLT-F and PLT-I is smaller than a predetermined value, e.g., if a value obtained from the PLT-I is almost same as the PLT-F, the next methodology can be switched (back) to the PLT-I detector, unless an unreliability of PLT-I counts in a current test is detected, as will be further described below.

If it has been found that the relationship is met, if one or more of the previous measurement value obtained from the PLT-I is almost the same (i.e. has a difference value smaller than a predetermined value) as the PLT-F as described above, then the blood analyzer is controlled to only prepare a first measurement sample and to subsequently only use the first detector (PLT-I) for the current detection time. This is despite the fact that in a previous measurement time both the first and second detectors have been used. An example of such a situation is illustrated in FIG. 12 for the patient 3 in case of the fifth detection time (on May 5, 2016) in which only the PLT-I detector is used despite the fact that on the previous detection time (on Apr. 5, 2016) both the PLT-I and the PLR-F detector have been used. This mechanism provides an increased cost effectiveness in the context of providing data with the same level of accuracy/reliability because it allows to go back and use only the first PLT-I detector which is less expensive than the PLT-F measurement.

On the other hand, if the relationship is not met, then both a first and second measurement sample should be prepared, as will be further described below.

Accordingly, in step S1602 of FIG. 13 the relationship is determined between at least one first measurement value obtained by detecting platelets in at least one previous test by an electrical type detector (first detector) of the blood analyzer and at least one second measurement value obtained by detecting the platelets in the at least one previous test by an optical type detector (second detector) of the blood analyzer. As detailed above, the determined relationship indicates a reliability of the one or more first measurement values obtained in the one or more previous test (measurements) based on a comparison with the one (or more) second measurement values.

Based on the determined relationship, in step S1603 of FIG. 13 the blood analyzer is controlled to prepare the first and/or second measurement sample. Subsequently, in step S1604, the blood analyzer is controlled to use the first and/or second detector for the respectively prepared first and/or second measurement sample. Based on such a control of the blood analyzer, the accuracy/reliability of the measurements may be made more consistent because measurement results are continuously provided which have the same level of accuracy/reliability. In other words, once the second PLT-F detector (which is more accurate than the PLT-I detector) has been used in a previous detection time, the second PLT-F detector is continuously used unless the first PLT-I detector has the same level of accuracy/reliability as the second PLT-F detector. In still other words, a continuous time series of detection results (at a plurality of continuous detection/measurement points) may be provided by the blood analyzer such that, for example in the context of a clinical environment, day-to-day fluctuations of platelet counts are attributable to actual changes of the number of platelets in a patient and not, incorrectly, due to the usage of different reliabilities of measurement methodologies. In a case of severe thrombocytopenia, accurate and consistent PLT counts are, for example, essential for platelet transfusion decision.

The above and below control processes may be performed by the controller 11 as illustrated in FIG. 7. The above and below control process may also be performed by the operation and display device 2, as shown above in FIGS. 1 and 8, preferably in interaction with the controller 11 in the analyzer body 1. In another preferred embodiment, the blood analyzer may also be controlled by another control device (also referred to as work area manager (WAM)). Such a preferred embodiment is illustrated in FIG. 15 which illustrates the first detector (electrical type detector, first measurement unit D1 (PLT-I)) and the second detector (electrical type detector, third measurement unit D3 (PLT-F)) in a communication connection with a first controller (which may comprise one or more information processing units (IPUs) according to the operation and display device 2 described above, preferably in interaction with the controller 11 of the analyzer body 11), for example a respective IPU for each measurement unit) and wherein the first controller is in a communication connection with a second controller (WAM). According to this preferred embodiment, an initial order for the measurement of platelets of a patient is received at the WAM from an external device (a laboratory information system (LIS)). Such an initial order may include, for example, only a CBC order. The CBC order includes orders for measurement items, such as red blood cell, white blood cell, hemoglobin and platelets (PLT-I). Here, the WAM stores the patient-specific detection history as described above in conjunction with FIG. 12, and both the WAM (second controller) and the IPU (first controller) control the blood analyzer based on the processed as described above in FIG. 13 and as further described below in FIG. 14. As such, the first and second controller provide a distributed control for the blood analyzer.

Figure 14:
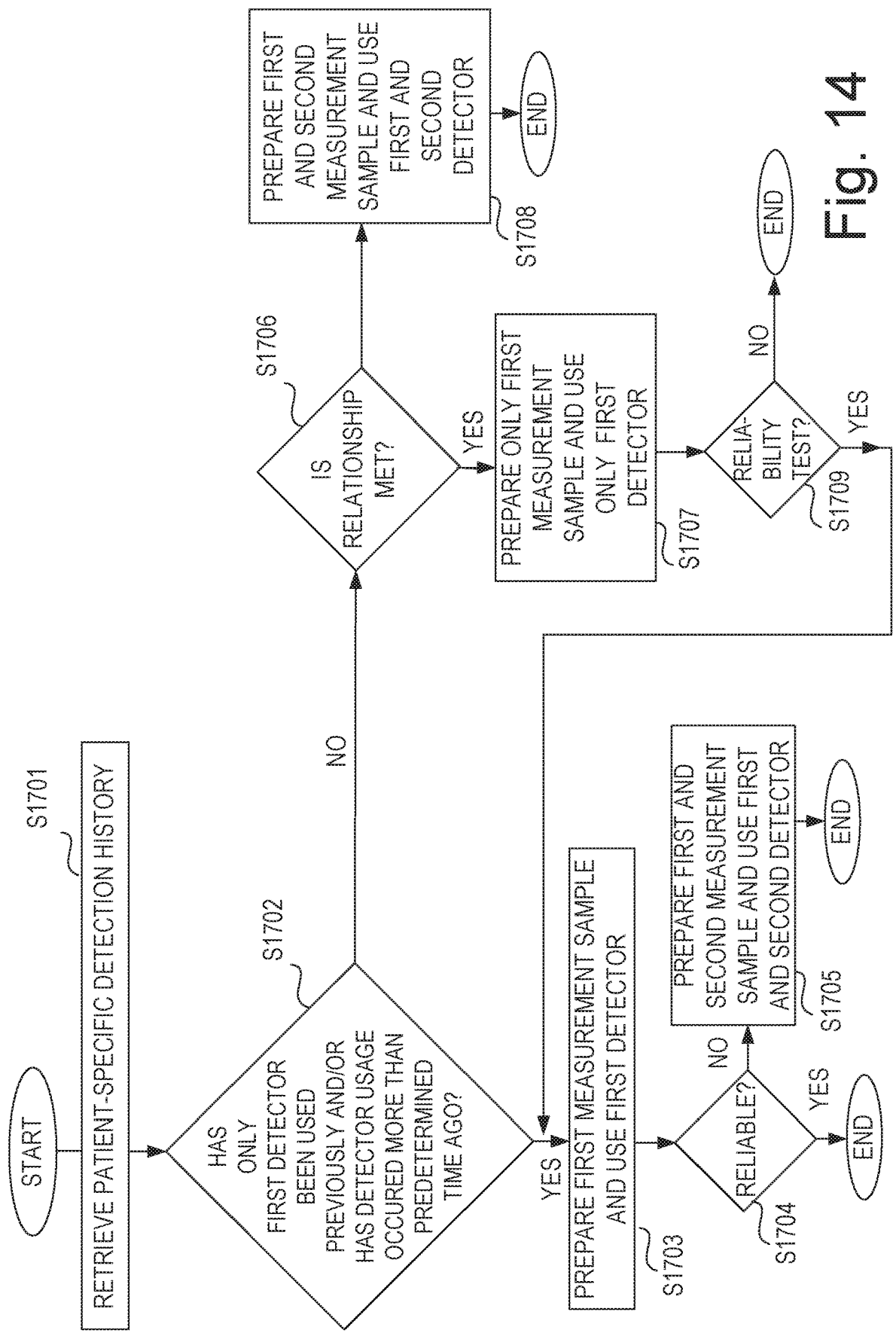
FIG. 14 is another flow chart showing the sequence of a method of controlling the blood analyzer according to the embodiment of the blood analyzer of the present invention.
Figure 15:
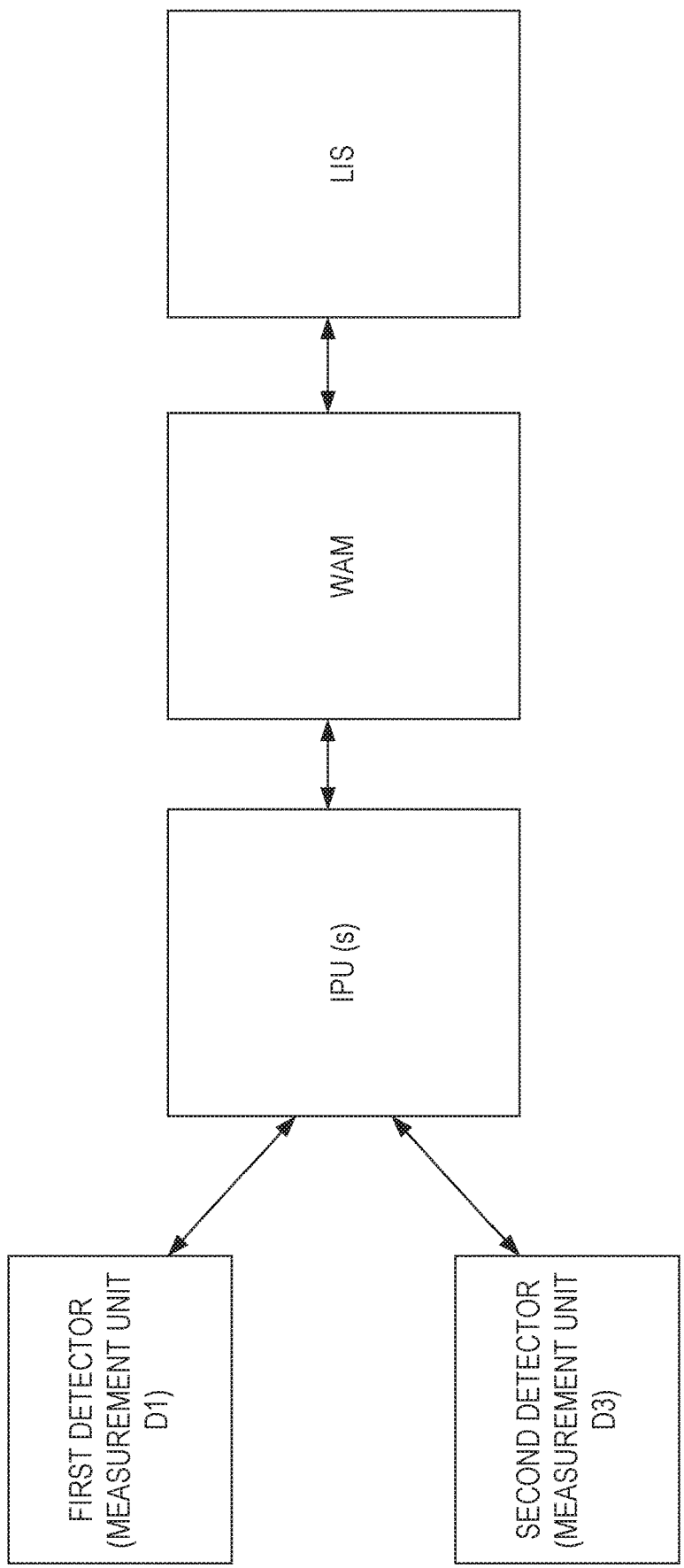
FIG. 15 shows a structure of a preferred embodiment of the blood analyzer of the present invention.

FIG. 14 illustrates another method for controlling the blood analyzer according to the present embodiment. Here, the second controller (WAM) may prepare/generate a measurement order for PLT-F according to the determined relationship (as described above) and transmits the measurement orders (which include the initial order and the generated order) to the first controller (IPU). The first controller may then return respective measurement results from the first and/or second detector to the WAM. The measurement results are appropriately stored in the patient-specific detection history, and may be further reported back to the LIS. Although FIG. 14 illustrates a distributed control based on the first and second controller as shown in FIG. 15, this is not considered as limiting. Instead, the control processes as shown in FIG. 14 may also be performed by the controller 11 of the analyzer body and/or the operation and display device 2 (IPU).

Referring back to FIG. 14, according to a first step S1701, as may be performed by WAM, a patient-specific detection history is retrieved from a database. This step is equivalent to step S1601 as explained above. In addition, the WAM may determine whether an initial order, as received from LIS, includes an order for a PLT-F measurement.

If the initial order includes only CBC order and does not include the order for the PLT-F measurement, in step S1702, which may be performed by WAM, a decision is made as to whether only the first detector PLT-I has been used in the previous detection time for determining the platelets for the specific patient, that is, whether PLT-F was not measured in the previous detection time. It is noted that, if the PLT-F methodology was used in the previous detection time (i.e. in the previous test), then also the PLT-I methodology was used because the PLT-F is always measured together with the CBC, which includes the PLT-I value. According to the patient-specific detection history, as illustrated in FIG. 12, such a case occurs, for example, for the patient 1 at the detection time Mar. 5, 2016 because on the (then) previous detection time Feb. 5, 2016 only the first detector PLT-I had been used which may be indicated by the PLT-I detection value. In such a case, i.e. if only the first detector PLT-I has been used in the previous detection time, WAM may send only the initial order to the IPU, and the blood analyzer is controlled in step S1703 by IPU, to prepare a first measurement sample and to use only the first detector for the current detection time.

Subsequently, in step S1704, which may be performed by IPU, a reliability determination on the current measurement result may be performed, as explained above in connection with FIG. 7. If it is determined in step S1704 that a reliability of the current detection result of the first detector is not sufficient, in step S1705, which may be performed by IPU, a first and second measurement sample is prepared and both the first and second detector for detecting the platelet component is used. It is noted that in step S1705 the first sample is again prepared and the first detector is again used to determine/derive other parameters such as a white blood cell count, the red blood cell count or the like from the first sample. A reason to again use the first detector may be based on the fact that a laboratory/user has a preference to always use measurement values from one measurement as otherwise a plurality of detection results would have to be compiled from different measurement. If it is determined in step S1704 that a reliability of the current detection result of the first detector is sufficient, the detection result (measurement values of PLT-I) is sent to WAM. The measurement value of PLT-I is stored as a test result of platelets in each memory device of WAM and the operation and display device 2. The test results of platelets stored in the memory device can be displayed on a display device of WAM and the operation and display device 2 for monitoring, for example, a change of the PLT count between current test and previous test.

It is noted that, in an alternative embodiment, in step S1705 a control process is performed, for example by IPU, to only prepare the second sample and to use only the second detector.

On the other hand, it may also be determined in step S1701 that a detection history is not yet present for a specific patient, for example in case of a very first measurement time. Then, the method for controlling the blood analyzer would initialize storing a detection history for such a new patient and move directly to step S1703.

In a preferred embodiment, it may be also or alternatively determined in step S1702, which may be performed by WAM, whether the previous detector usage has occurred at a time point that differs from the current time point by more than a predetermined time period, for example 3 days. In such a case, the method always proceeds with step S1703 as explained above.

Further, according to step S1706 of the method according to FIG. 14, which may be performed by WAM, it is determined whether the relationship (as explained above) between a first measurement value obtained by detecting the platelets in one or more previous detection times by the first detector (PLT-I) and a second measurement value obtained by detecting the platelets in one or more previous detection time by the second detector (PLT-F) is met. If then, according to step S1706 of FIG. 14, it has been found that the relationship is met, e.g. if one or more of the previous value(s) has a difference value smaller than a predetermined value, and the relationship thus indicates that the at least one first measurement value in the at least one previous test is reliable, then the blood analyzer is controlled in step S1707, which may be performed by IPU or WAM, to only prepare a first measurement sample and to only use the first detector (PLT-I) for the current detection time. This is despite the fact that in a previous measurement time both the first and second detectors have been used (as has been determined in step S1702). An example of such a situation is illustrated in FIG. 12 for the patient 3 in case of the fifth detection time (on May 5, 2016) in which only the PLT-I detector is used despite the fact that on the previous detection time (on Apr. 5, 2016) the PLT-F detector has been used. This mechanism provides increased cost effectiveness in the context of providing data with the same level of accuracy because it allows to go back and use only the first PLT-I detector which is less expensive than the PLT-F measurement.

In a preferred embodiment, as illustrated in step S1709 of FIG. 14, which may be performed by WAM or IPU, it may be determined whether a reliability test for the current measurement result (i.e. the current test) as obtained in step S1707 by using only the first detector (PLT-I) should additionally be performed. Such a decision may be based on a user setting of the blood analyzer or the like. It may also be based on the setting of the relationship/criterion, for example in case of a selection of a specific criterion that should be associated with a subsequent reliability test. In other words, the subsequent reliability test for the current test in step S1709 could be inactivated under certain conditions. If, based on the above, it is determined in step S1709 not to perform a subsequent reliability test, then it is decided in the control process that the value obtained from the first detector (PLT-I) may be used even though the second detector (PLT-F) was used for at least one of the previous detection times. If, on the other hand, it is determined in step S1709 to perform a subsequent reliability test, then the process flow moves to step S1704 as explained above. As such, even though the relationship/criterion is met in step S1706 detection results as acquired by both the first and second detector may be acquired if the reliability still cannot be guaranteed in step S1704. Such an additional reliability processing may further improve the accuracy of the control process and avoid missing new clinical situations.

If on the other hand, according to step S1706 of FIG. 14, it has been found that the relationship is not met, i.e. when the relationship does not indicate that the at least one first measurement value in the at least one previous test is reliable, then WAM may generate a new measurement order for PLT-F and may send both the initial order and the generated new measurement order to IPU to control the blood analyzer The blood analyzer is thus controlled in step S1708, which may be performed by IPU, to prepare the first and the second measurement sample in one step. In other words, the first and the second measurement samples are prepared in a single step in which an aspirated sample is divided into two aliquots. That is, by using a single aspiration process for providing both the first and second measurement sample, and to subsequently use both the first PLT-I detector and the second PLT-F detector. Such a step does not introduce a time delay, as compared to steps S1703-S1705 in which the patient-specific sample has to be provided in a stand-by state for a subsequent aspiration process to prepare the second measurement sample. In other words, even if there is no initial order for a PLT-F measurement, when the difference between the previous PLT-F and PLT-I for the specific patient who is currently subject of the measurement is significantly large, a measurement order for PLT-F is generated and the controller is operated to obtain a PLT value based on the PLT-F.

According to the present embodiment, the proper methodology (PLT-I or PLT-F) may therefore be selected for the blood analyzer in order to compare platelet counts from the same patient obtained at different time points: in case the difference between PLT-I and PLT-F from the previous sample is large, as described above, a PLT-F measurement is immediately triggered without an initial PLT-I measurement. However, if previously both PLT-F and PLT-I were measured but the resulting values were similar, no automatic PLT-F measurement is performed in order to avoid unnecessary PLT-F measurements. This will lead to improved monitoring of platelet counts in thrombocytopenic patients because comparable platelet counts are evaluated. In addition, unnecessary additional costs due to PLT-F measurements are prevented.

While the present embodiment has been described above as using PLT-I as first detection methodology of an "impedance platelet count" and PLT-F as a second detection methodology of an a "fluorescence flow cytometry", the present invention is not limited in that regard. For example, in a first variation, the fluorescence flow cytometry may be based on one of PLT-F, PLT-O (a fluorescent PLT count obtained from the RET channel of Sysmex analyzers) and immune flow cytometry methods such as the use of CD41 and/or CD61 antibodies, or may be based on a combination of PLT-F, PLT-O and immune flow cytometry.

In addition, the present embodiment may be further supplemented by a determination as to whether there are platelet clumps. Platelet clumps may, for example, be detected using a method as described in U.S. Pat. No. 7,923,229. Such a determination may be performed after the sample(s) have been prepared, such as after steps S1602 or S1603 shown in FIG. 13, or alternatively during the control process, for example after steps S1703, S1705, S1707 or 1708 in FIG. 14. Samples with signs of platelet clumps are considered as unreliable and lead to a termination of the control process.

What is claimed is:

1. A method of controlling a blood analyzer for measuring platelets, comprising:

determining, by a controller, whether, for measuring platelets, an electrical detector of the blood analyzer has been used and an optical detector of the blood analyzer has not been used or both the electrical detector and the optical detector have been used in a first test based on patient history information, wherein the first test occurs before a second test;

in response to determining that both the electrical detector and the optical detector have been used in the first test, determining, by the controller, a difference in measurement values by comparing at least one first measurement value with at least one second measurement value, wherein the first measurement value is a count of platelets in a blood sample of a patient in the first test by the electrical detector, and the second measurement value is a count of the platelets in the blood sample of the patient in the first test by the optical detector, and wherein the electrical detector comprises a flow cell, a pair of electrodes provided with the flow cell, and a power source supplying a direct current to the electrodes;

in response to determining that the difference in measurement values is less than a predetermined value, controlling, by the controller, the blood analyzer to prepare a first measurement sample for the electrical detector and to use the electrical detector for the second test;

in response to determining that the difference in measurement values is greater than or equal to the predetermined value, controlling, by the controller, the blood analyzer to prepare both the first measurement sample for the electrical detector and a second measurement sample for the optical detector and to use both the electrical detector and the optical detector for the second test;

determining whether the second test occurs within a predetermined amount of time after the first test; and in response to determining that the second test does not occur within the predetermined amount of time after the first test, controlling, by the controller, the blood analyzer to prepare the first measurement sample for the electrical detector and to use the electrical detector for the second test.

2. The method of claim 1, wherein the method further comprises:
in response to determining that only the electrical detector has been used in the first test, controlling, by the controller, the blood analyzer to prepare the first measurement sample and to use the electrical detector for the second test.

3. The method of claim 1, wherein the method further comprises:
when the count of platelets detected by the electrical detector in the second test is equal to or greater than the predetermined value, determining that a first measurement value is accurate.

4. The method of claim 1, wherein determining the difference in measurement values further comprises:
when the difference between the first measurement value and the second measurement value is less than the predetermined value, determining that the first measurement value is accurate in the first test.

5. The method of claim 1, wherein the method further comprises:
when it is determined that both the electrical detector and the optical detector have been used in the first test, storing the second measurement value in the first test, to a memory; and
when only the first measurement sample is prepared for the second test, storing a first measurement value in the second test to the memory.

6. The method of claim 1, wherein determining the difference in measurement values comprises:
determining, by the controller, the difference in measurement values by comparing the at least one first measurement value with the at least one second measurement value in response to:
determining that both the electrical detector and the optical detector have been used in the first test; and
determining that the second test occurs within the predetermined amount of time after the first test.

7. A controller of a blood analyzer for measuring platelets, wherein the controller is configured to:
determine whether, for measuring platelets, an electrical detector of the blood analyzer has been used and an optical detector of the blood analyzer has not been used or both the electrical detector and the optical detector have been used in a first test based on patient history information, wherein the first test occurs before a second test;

in response to determining that both the electrical detector and the optical detector have been used in the first test, determine a difference in measurement values by comparing at least one first measurement value with at least one second measurement value, wherein the first measurement value is a count of platelets in a blood sample of a patient in the first test by the electrical detector, and the second measurement value is a count of the platelets in the blood sample of the patient in the first test by the optical detector, and wherein the electrical detector comprises a flow cell, a pair of electrodes provided with the flow cell, and a power source supplying a direct current to the electrodes;

in response to determining that the difference in measurement values is less than a predetermined value, control the blood analyzer to prepare a first measurement sample for the electrical detector and to use the electrical detector for the second test;

in response to determining that the difference in measurement values is greater than or equal to the predetermined value, control the blood analyzer to prepare both the first measurement sample for the electrical detector and a second measurement sample for the optical detector and to use both the electrical detector and the optical detector for the second test;

determine whether the second test occurs within a predetermined amount of time after the first test; and in response to determining that the second test does not occur within the predetermined amount of time after the first test, control the blood analyzer to prepare the first measurement sample for the electrical detector and to use the electrical detector for the second test.

8. The controller of claim 7, wherein the controller is further configured to:
store, to a database, whether the electrical detector has been used or both the electrical detector and the optical detector have been used for the first test for detecting the platelets.

9. The controller of claim 7, wherein the controller is further configured to:
in response to determining that only the electrical detector has been used in the first test, control the blood analyzer to prepare the first measurement sample and to use the electrical detector for the second test.

10. The controller of claim 7, wherein the controller is further configured to:
when the count of platelets detected by the electrical detector in the second test is equal to or greater than the predetermined value, determine that a first measurement value is accurate.

11. The controller of claim 7, wherein, when determining the difference in measurement values, the controller is configured to:
determine the difference in measurement values by comparing the at least one first measurement value with the at least one second measurement value in response to:
determining that both the electrical detector and the optical detector have been used in the first test; and determining that the second test occurs within the predetermined amount of time after the first test.

12. A blood analyzer for measuring platelets, comprising
a sample preparing section comprising a plurality of mixing chambers and configured to prepare a first measurement sample for measurement of platelets by an electrical measurement and to prepare a second measurement sample for measurement of platelets by an optical measurement;
an electrical detector configured to detect platelets in the first measurement sample, wherein the electrical detector comprises a flow cell, a pair of electrodes provided with the flow cell, and a power source supplying a direct current to the electrodes;
an optical detector configured to detect platelets in the second measurement sample; and
a controller configured to:
  determine whether, for measuring the platelets, the electrical detector has been used and an optical detector of the blood analyzer has not been used or both the electrical detector and the optical detector have been used in a first test based on patient history information, wherein the first test occurs before a second test;
  in response to determining that both the electrical detector and the optical detector have been used in the first test, determine a difference in measurement values by comparing at least one first measurement value with at least one second
measurement value, wherein the first measurement value is a count of platelets in a blood sample of a patient in the first test by the electrical detector, and the second measurement value is a count of the platelets in the blood sample of the patient in the first test by the optical detector;
  in response to determining that the difference in measurement values is less than a predetermined value, control the blood analyzer to prepare the first measurement sample for the electrical detector and to use the electrical detector for the second test;
  in response to determining that the difference in measurement values is greater than or equal to the predetermined value, control the blood analyzer to prepare both the first measurement sample for the electrical detector and the second measurement sample for the optical detector and to use both the electrical detector and the optical detector for the second test;
  determine whether the second test occurs within a predetermined amount of time after the first test; and
  in response to determining that the second test does not occur within the predetermined amount of time after the first test, control the blood analyzer to prepare the first measurement sample for the electrical detector and to use the electrical detector for the second test.

13. A computer-readable storage medium having a program recorded thereon, the program to direct a processor to perform acts of:
determining whether, for measuring platelets, an electrical detector of a blood analyzer has been used and an optical detector of the blood analyzer has not been used or both the electrical detector and the optical detector have been used in a first test based on patient history information, wherein the first test occurs before a second test;
in response to determining that both the electrical detector and the optical detector have been used in the first test, determining a difference in measurement values by comparing at least one first measurement value with at least one second measurement value, wherein the first measurement value is a count of platelets in a blood sample of a patient in the first test by the electrical detector, and the second measurement value is a count of the platelets in the blood sample of the patient in the first test by the optical detector, and wherein the electrical detector comprises a flow cell, a pair of electrodes provided with the flow cell, and a power source supplying a direct current to the electrodes;
in response to determining that the difference in measurement values is less than a predetermined value, controlling the blood analyzer to prepare a first measurement sample for the electrical detector and to use the electrical detector for the second test;
in response to determining that the difference in measurement values is greater than or equal to the predetermined value, controlling the blood analyzer to prepare both the first measurement sample for the electrical detector and a second measurement sample for the optical detector and to use both the electrical detector and the optical detector for the second test;
determining whether the second test occurs within a predetermined amount of time after the first test; and
in response to determining that the second test does not occur within the predetermined amount of time after the first test, controlling the blood analyzer to prepare the first measurement sample for the electrical detector and to use the electrical detector for the second test.

\* \* \* \* \*